United States Patent [19]

Bachet et al.

[11] Patent Number: 4,567,345

[45] Date of Patent: Jan. 28, 1986

[54] PROCESS AND APPARATUS FOR THE IN-LINE INSPECTION OF THE DEPTH OF A WELD BY A PULSE BEAM

[75] Inventors: Bernard Bachet, Marsonnay la Côte; Jean Daguet, Dijon; Louis Dujardin, Fontaine les Dijon, all of France

[73] Assignee: Commissariat a l'Energie Atomique, Paris, France

[21] Appl. No.: 560,580

[22] Filed: Dec. 12, 1983

[30] Foreign Application Priority Data

Dec. 17, 1982 [FR] France .................. 82 21206

[51] Int. Cl.$^4$ ................................ B23K 9/00
[52] U.S. Cl. .................. 219/121 PT; 219/121 PC; 219/121 PY; 156/626
[58] Field of Search ...... 219/121 P, 121 PY, 121 LB, 219/121 LX, 121 EW, 121 EY, 130.01, 121 EM, 121 PT, 121 PC; 156/626, 627; 73/432 C, 432 CR

[56] References Cited

U.S. PATENT DOCUMENTS

| | | | |
|---|---|---|---|
| 3,271,558 | 9/1966 | Davis | 219/130.01 |
| 3,974,381 | 8/1976 | Rohrle et al. | 219/121 EY |
| 4,127,762 | 11/1978 | Paton et al. | 219/121 EM |

FOREIGN PATENT DOCUMENTS 2076185 10/1971 France .
2158320 6/1973 France .

OTHER PUBLICATIONS

Apr. 1981—Laser Focus, vol. 17, No. 4, pp. 30–34, entitled "Laser Assesses Weld Composition to Evaluate Condition of Reactors", (Author unknown).

Mar. 1976—Laser Focus, vol. 12, No. 3, pp. 33–36, entitled "Automated Welding of Minute Parts", by J. Aeschlimann et al.

Feb. 1982—IBM Technical Disclosure Bulletin, vol. 24, No. 9, pp. 4691–4692, entitled "Closed-Loop Laser Control System", by H. E. Klauser.

Primary Examiner—C. L. Albritton
Assistant Examiner—M. N. Lateef
Attorney, Agent, or Firm—Cesari and McKenna

[57] ABSTRACT

A process for the in-line inspection of the depth of a weld carried out by a welding beam pulse in which around its impact point on a workpiece, the beam pulse produces a welding plasma wherein, only during the emission of a welding beam pulse, at least one selected monochromatic emission line of the welding plasma is optically collected from the workpiece. The energy of said lines is converted into analog electrical signals and those signals are digitally processed with the resulting signals being compared with reference signals to produce an indication of the weld depth. Apparatus for performing this process is also disclosed.

10 Claims, 4 Drawing Figures

PROCESS AND APPARATUS FOR THE IN-LINE INSPECTION OF THE DEPTH OF A WELD BY A PULSE BEAM

BACKGROUND OF THE INVENTION

The present invention relates to a process and an apparatus for the in-line inspection of the depth of a weld by means of a pulse beam. In line inspection is understood to mean that inspection takes place at the same time as the welding operation. It is more particularly used in inspecting shallow welds.

The Expert is aware of numerous methods for inspecting or controlling the depth of a weld. The most frequently encountered methods are based on ultrasonics, eddy currents, potentiometry and absorption spectrometry.

In the ultrasonic method, it is necessary to use a frequency such that the propagation of the ultrasonics, without exaggerated losses, requires the use of a fluid called a "coupling fluid". Thus, the ultrasonic method cannot be used in the case of an in-line inspection, because the coupling fluid necessary for this method is destroyed by the welding beam.

The eddy current method and the potentiometric method for inspecting the depth of a weld have common disadvantages. These two methods make it necessary to move close to the welding point of the probes, in the case of the eddy current method, or the electrodes in the case of the potentiometric method. The precise positioning of these probes is difficult and can also be prejudicial to the weld.

The method for inspecting the depth of a weld by the absorption of a line operates in the following way. A monochromatic radiation source is placed in a welding enclosure containing the part to be welded and the welding beam and said monochromatic radiation is directed against the welding plasma. This monochromatic source is generally a hollow cathode lamp. A fraction of the emitted radiation is absorbed by the particles present in the welding plasma. These particles are supplied to the part to be welded (tracer method) or are present in the part to be welded in the form of impurities (autotracer method). They are released in the welding plasma by the welding beam. The number of particles released and consequently the fraction of the monochromatic radiation absorbed is proportional to the depth of the weld. The depth of the weld is then evaluated by comparison between the level of the collected signal and the level of a reference signal.

The monochromatic radiation source cannot be used continuously. Thus, in this case, the signal collected in the optical means is constituted by the unabsorbed fraction of the monochromatic radiation, on which is superimposed an emission radiation due to the welding plasma. However, the emission of the welding plasma has a much higher level than the emission of the monochromatic radiation. Consequently, the useful signal disappears in a background noise and cannot be used.

In order to obviate this problem, it is necessary to break down the monochromatic signal into a pulse beam and to carry out a synchronous detection. In the case of welding by a continuous beam, such as an electron beam, the frequency of the monochromatic signal is e.g. 500 Hz. In the case of welding by a pulse beam, it is at the level of each welding pulse that the monochromatic source must emit a large number of pulses. For a welding pulse beam, such as a laser beam supplying e.g. pulses lasting 4 ms every 100 ms, the frequency of the pulses of the monochromatic source must be roughly a few kilohertz so that, during each welding beam pulse, the monochromatic pulse source emits about 100 pulses. The Expert does not have simple means making it possible to easily realise such a monochromatic pulse beam.

No known inspection method consequently makes it possible to carry out an in-line inspection of the depth of a weld by a pulse beam and which is simple, reliable and accurate. The object of the invention is to provide a process and an apparatus enabling such an inspection to be carried out.

SUMMARY OF THE INVENTION

The present invention specifically relates to a process for the in line inspection of the depth of a weld carried out by a pulse beam in which, around its impact point on the part to be welded, the pulse beam produces a welding plasma, wherein for each welding beam pulse is collected at least one emission line of the welding plasma in an optical means, wherein the energy of these lines is converted into analog electrical signals, wherein these signals are digitally processed and wherein the signals resulting from the digital processing are compared with reference signals.

According to a secondary feature, by means of a control loop, the power of the in-line welding pulse beam is controlled by a signal depending on the difference between the level of the signals resulting from the digital processing and the level of the reference signals.

This control loop makes it possible to make a weld of constant depth.

The invention also relates to an apparatus for the in line inspection of the depth of a weld by a pulse beam, in which the part to be welded and the welding means supplying a pulse beam are contained in a welding enclosure, wherein it comprises at least one measuring channel, each constituted by an optical means for collecting the radiation emitted by the welding plasma, said optical means being located in the welding enclosure, a monochromator connected to the optical means by a transmission means, a photomultiplier connected to the monochromator and incorporating, apart from the measuring channel, means for processing the electrical signals from the photomultipliers and means for displaying the signals from the processing means and means for comparing these signals with reference signals.

According to a secondary feature, the apparatus comprises an in-line control loop using a signal supplied by an output of the comparison means controlling the intensity of the welding pulse beam.

According to another secondary feature, each optical means receives the end of an optical fibre. The use of the end of an optical fibre as the means for receiving the radiation emitted by the plasma makes it possible to limit the overall dimensions in the welding enclosure.

According to another secondary feature, each optical means comprises optical lenses and mirrors. An optical means comprising lenses and mirrors can be more easily used than an optical means comprising the end of an optical fibre, but it has larger dimensions.

According to another feature, each optical means also comprises a collimator, which makes it possible to improve the sensitivity of the optical means.

According to another feature, the measuring channels are paired and the apparatus comprises a regulating means making it possible to render equal the optoelectronic efficiency of the measuring channels of the same pair. Through making equal the optoelectronic efficiency of the two measuring channels it is possible to compare the signals received by each of these channels and to carry out correlations on the signals, which improve the quality of the information contained in the collected signals.

According to another embodiment, the regulating means is constituted by a radiation source emitted the same radiation in each of the measuring channels of the same pair. This source can be of a random nature, provided that it emits a radiation of a sufficient intensity for the processing means to receive a signal having a usable level.

According to another secondary feature, the processing means comprises a means for standardizing the signals received from the measuring channels, a recorder making it possible to effect a delayed processing of these signals, a band-pass filter, a time filter, an analog-digital converter and an arithmetic unit.

BRIEF DESCRIPTION OF THE DRAWINGS

The invention is described in greater detail hereinafter relative to non-limitative embodiments and the attached drawings, wherein show.

DETAILED DESCRIPTION OF THE INVENTION

Figure 1:
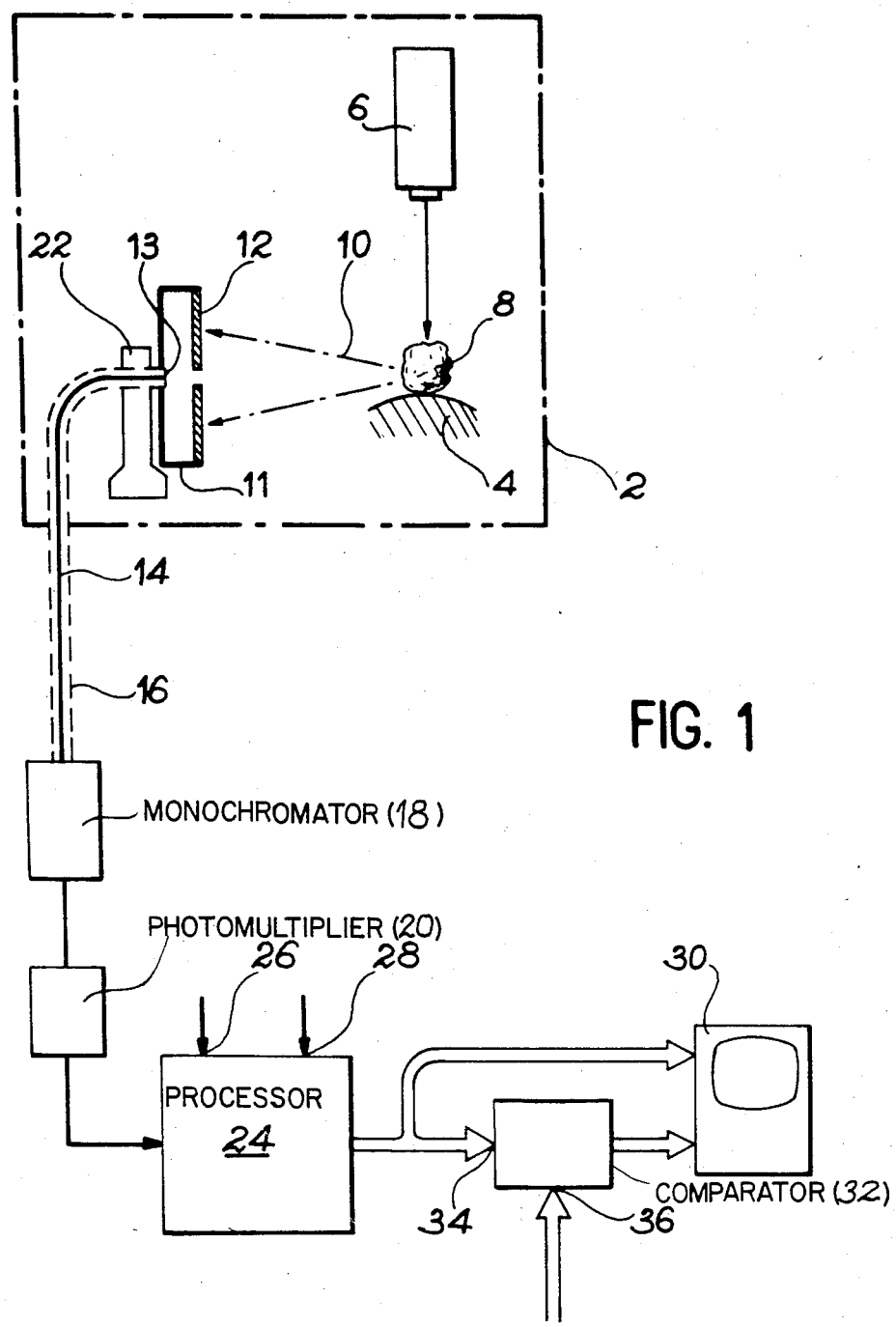
FIG. 1 a first embodiment of the apparatus having a single measuring channel.

FIG. 1 shows an embodiment of the control or inspection apparatus according to the invention with a single measuring channel. A welding enclosure 2 contains the part 4 to be welded and the welding means 6 supplying a pulse beam producing a welding plasma 8 around its impact point on the part 4. The radiation 10 emitted by this welding plasma 8 is intercepted and then converted into an electrical signal by a measuring channel incorporating an optical means 11 for collecting the radiation 10 emitted by the welding plasma 8, a transmission means 14 passing the light radiation intercepted outside the welding enclosure 2 towards the other elements of the measuring channel, a monochromator 18 and a photomultiplier 20.

The optical means 11 for collecting the light beam 10 from welding plasma 8 comprises a collimator 12, so that only part of the beam from welding plasma 8 is collected. This permits a better sensitivity. This is because two welding plasmas of the same volume, one deep and narrow, the other shallow and wide emit a radiation of the same intensity. The use of a collimator like 12 makes it possible to collect the emission from a given plasma surface area and consequently make a distinction between deep and shallow plasmas. This is because the collected energy will be more intense in the case of the deep plasma. The optical means 11 also comprises a means making it possible to direct the beam which has traversed collimator 12 to the input of the transmission means 14. In the present case, where the transmission means 14 is constituted by an optical fibre, said means is constituted by the end 13 of this optical fibre. In order that this signal transmitted by optical fibre 14, protected by sheath 16 can be compared with a reference signal, it is necessary that the operating conditions under which the signal has been collected are the same as those under which the reference signal was collected. Thus, in both cases, it is necessary to ensure the same efficiency of the optical means 12 for collecting radiation 10. This more particularly makes it necessary for the end 13 of optical fibre 14 to be exactly in the same position in both cases. This can be ensured by a support 22. If it is not sure whether the position of end 13 of optical fibre 14 is the same during acquisition of the reference signal and during acquisition of the signal, it is possible to replace end 13 by conventional optical means, such as mirrors and lenses. However, the optical efficiency of optical means 12 is slightly less advantageous in this case.

Monochromator 18 located at the end of transmission means 14 makes it possible to select one of the lines of the welding plasma emission spectrum. This line is chosen in a preferential manner from among the high intensity lines and among the emission lines of the major constituents of the part 4 to be welded. If the intensity of the lines of the major constituents of the part 4 to be welded saturates the measuring means, it is possible to use the lines of other constituents of part 4 to be welded. For example, if said part 4 is made from steel, the lines selected by monochromator 18 could be one of the lines of iron, nickel or chromium. The monochromator signal from monochromator 18 is then applied to a photomultiplier 20, which amplifies it and converts it into an electrical signal.

This electrical signal is then applied to the input of processing means 24, which also receives at its input 26 a signal, whose intensity is proportional to the power of the pulse beam and another signal at its input 28, which is active on the rising front of each welding pulse. The signal applied to input 16 would, for example, come from the power supply of welding means 6 or a fraction of the welding beam deflected by an adequate means. The signal applied to input 28 is used as the synchronization signal for the processing of the signal from the measuring channel. The processing means 24 carried out different operations on the signal received from photomultiplier 20. These operations will be defined in connection with the description of FIG. 4. At its output, it supplies one or more signals, which can either be directly transmitted to a display means 30, constituted in known manner by a display screen, a tracing table, etc, or to a comparison means 32. Thus, the comparison means receives on one of its inputs 34, the signal or signals from processing means 24 and on its other inputs 36, the reference signal or signals. From the comparison of these different signals, the comparison means deduces the depth of the weld made. The result can be transmitted to the display means 30.

Figure 2:
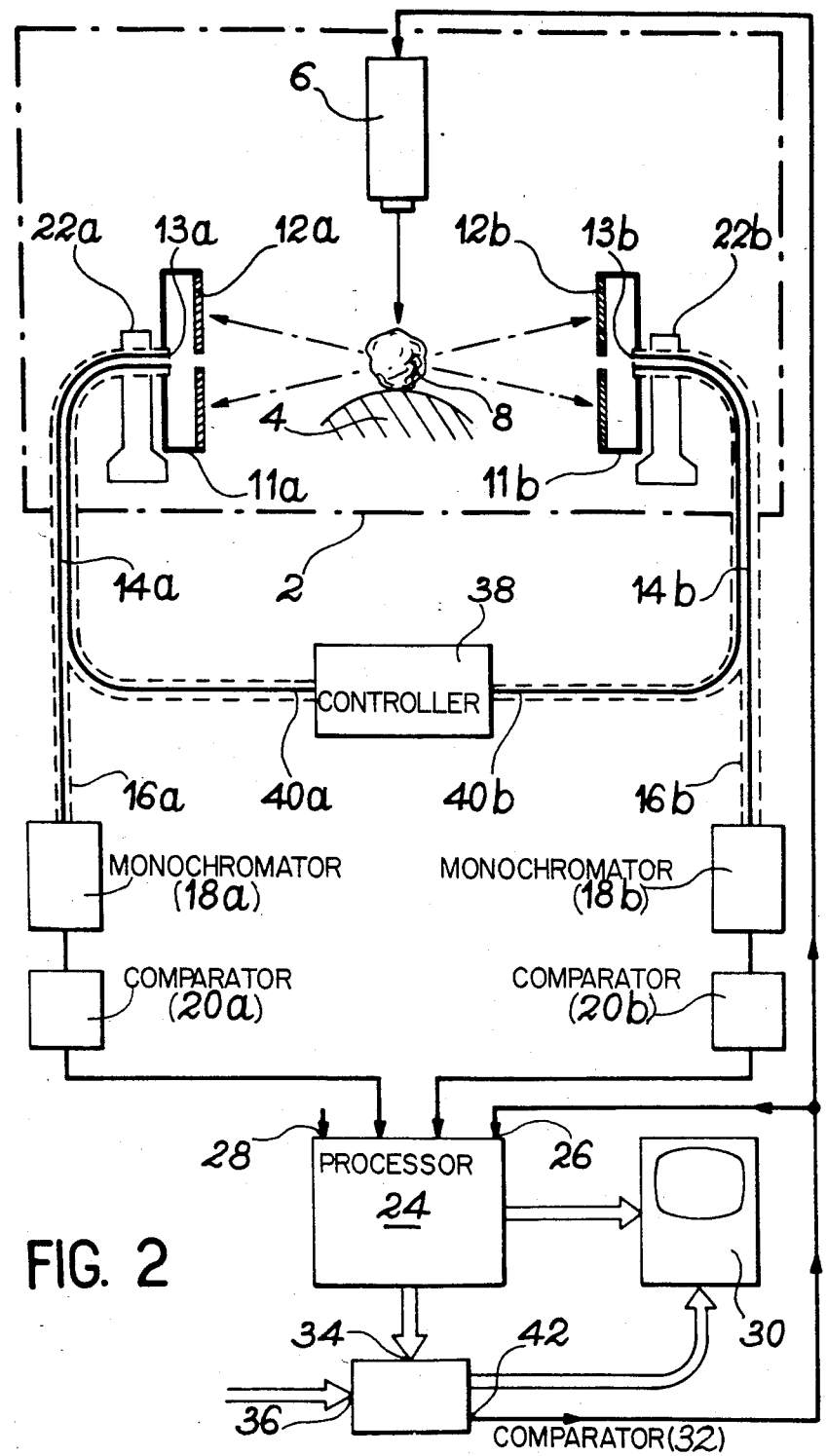
FIG. 2 another embodiment of the apparatus with two measuring channels and a control loop.

FIG. 2 shows another embodiment of the apparatus according to the invention and those elements already described in connection with FIG. 1 will not be described again. This apparatus has two basic differences compared with that of FIG. 1. It is equipped with two measuring channels and the comparison means supplies, in line, a signal making it possible to regulate the power of the welding means 6. The use of two measuring channels instead of 1 makes is possible to select two lines of the welding plasma 8 and consequently obtain better quality information. Thus, it is then possible to carry out a correlation between the information collected by each of the measuring channels. In order that the signals collected by each of the measuring channels can be compared in processing means 24, it is necessary for the two measuring channels to have the same optoelectronic efficiency. This will be measured and, if necessary, corrected by a control means 38.

The operating process of control means 38 is as follows. Control means 38 emits high power light radiation, produced e.g. by a xenon lamp, in each of the optical fibres 40a and 40b. The beam transmitted by fibre 40a travels in sheath 16a up to its end 13a. It then passes through collimator 12a, collimator 12b and enters fibre 14b by end 13b of sheath 16b. This signal then traverses monochromator 18b, then photomultiplier 20b is applied to one of the inputs of the processing means. In the same way, the light signal passing through fibre 32b then appears in fibre 14a and after passing through monochromator 18a and photomultiplier 20a, it is then applied to one of the inputs of processing means 24. The level of these two signals apply to the processing means 24 or their difference is then indicated to the user, e.g. on display means 30. The user then regulates the gain of the monochromators or photomultipliers or the positioned of the end 13a or 13b of the optical fibres, in such a way that the two signals received by the processing means 24 are of the same intensity level. The optoelectronic efficiency of each of the measuring channels is equal, so that control means 38 is stopped and welding can commence.

As in the embodiment of the previous drawing, the monochromatic signal supplied by each measuring channel is applied to one of the inputs of processing means 24, which also receives a signal applied to its input 26 proportional to the power of the pulse beam of welding means 6 and another signal applied to its input 28, which is activated on the rising front of each of the pulses of the pulse beam of welding means 6.

Figure 4:
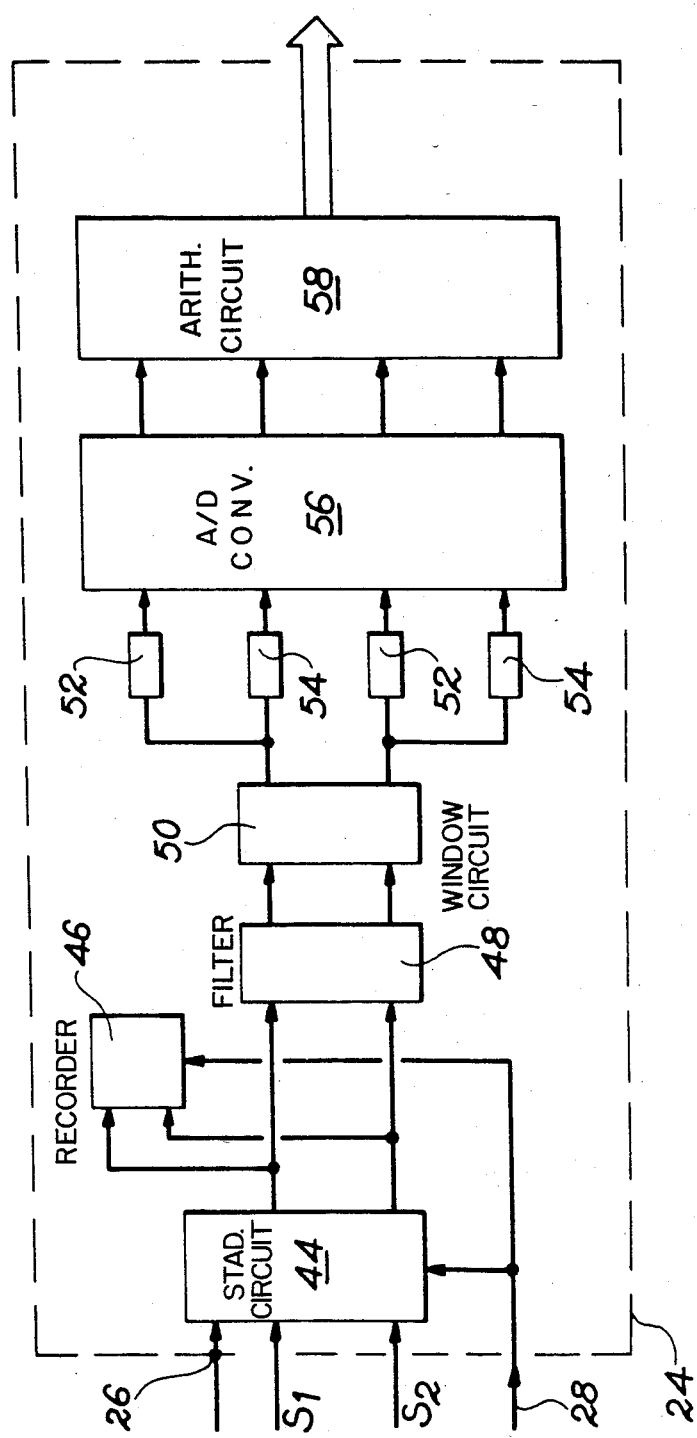
FIG. 4 a block diagram of the processing means.

The different operations which will be described in greater detail in connection with the description of FIG. 4 are carried out by processing means 24 on these various signals. Display means 30 is identical to the display means of the previous embodiment. Comparison means 32, as in the embodiment of the previous drawing, receives at its input 34 one or more signals from processing means 24 on the one hand and at its input 36 one or more reference signals and at its output supplies signals which are transmitted to the display means 30. It also supplies at an output 42 a signal, dependent on the result of the comparison made on signals received on each of its inputs, controlling the power of the pulse beam of welding means 6. This signal constitutes a return loop and makes it possible to carry out the in-line modification of the power of the pulse beam of welding means 6.

Figure 3:
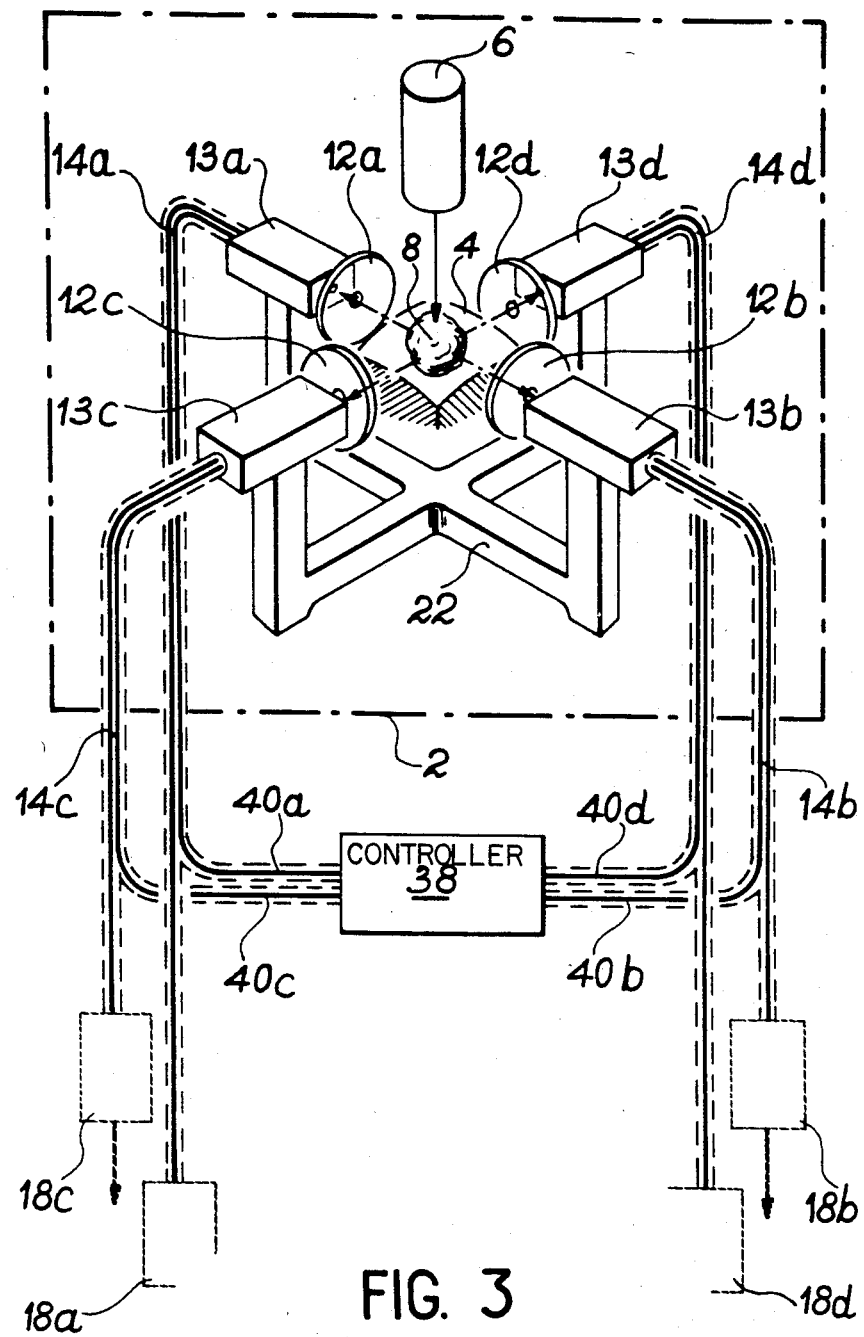
FIG. 3 another embodiment of the apparatus with four measuring channels and control loop.

FIG. 3 shows a special embodiment of the apparatus with four measuring channels. The increase in the number of measuring channels leads to a better quality of the information obtained. However, it is obvious that the cost of the apparatus and the overall dimensions in welding enclosure 2 increase with the number of measuring channels. The choice of the number of welding channels is consequently a compromise and will depend on the criteria adapted. It is not possible to regulate the efficiency of these measuring channels in such a way that it is identical for all four. It would then be necessary for each of the optical means 11 for collecting the light radiation to be related to all the other optical light ray collection means. Thus, the measuring channels are merely paired. In the arrangement shown in FIG. 3, it is possible to regulate to the same level the optoelectronic efficiency of measuring channels A and B, on the one hand, and that of channels C and D on the other. It is possible to consider the use of a regulating or control means, such as means 38 for each pair of measuring channels. However, it is less expensive to only use a single regulating means 38 for both pairs of measuring channels, or in general terms for N pairs of measuring channels. In the manner shown in FIG. 3, this can be brought about by connecting the optical fibres 40a and 40c to the same regulating means 38 and doing the same for optical fibres 40b and 40d. It is obvious that this arrangement is simpler than the arrangement requiring the same number of regulating means 38 as there are pairs of measuring channels. However, it is more difficult to put into effect, because it must be ensured that two paired channels such as 40a and 40b receive the same light intensity from regulating means 38.

FIG. 4 is a block diagram of processing means 24, which corresponds to an apparatus having two measuring channels. At two inputs, the processing means 24 receives signals $S_1$ and $S_2$ from the measuring channels. At its input 26, it also receives a signal proportional to the power of the pulse beam of welding means 6. At its input 28, it also receives an active signal on the rising front of each pulse from welding means 6. The latter signal acts as a synchronization signal. The first three signals are applied to the inputs of a standardization circuit 44. These three signals can then be directed to a recorder 46 to permit a delayed processing. They are then stored in parallel, e.g. on magnetic tape. If it is wished to carry out an in line inspection, the signals from circuit 44 are applied to the inputs of a filtering circuit 48, constituted by an adjustable band-pass filter. The signals from filter 48 are then applied to the two inputs of a circuit 50. The latter is a data or time window making it possible to only sample part of the signals present during the duration of the pulses of the pulse beam from welding means 6. More specifically, if $t_1$ and $t_2$ are the dates of the start and finish of the pulse of the welding pulse beam, the window will make it possible to pass through the signals applied to the input of circuit 50 between dates $t_3$ and $t_4$, verifying $t_1 \leq t_3 < t_4 \leq t_2$, the values of $t_3$ and $t_4$ being adjustable. At the output of circuit 50, the peak and integral values of each of the signals are detected, respectively by circuits 52 and circuits 54. The four values obtained are then applied to the input of an analog-digital converter 56. Digitized in this way, it is possible to carry out processing operations on these different values such as the sliding means, i.e. the mean on the N last values of a signal, the sum of the signals, the ratio of the two signals, etc. These processing operations are carried out by an arithmetic unit 58, which at the output supplies one or more signals making it possible to determine the depth of the weld, by comparison with the reference signals.

What is claimed is:

1. A process for the in-line inspection of the depth of a weld carried out by a pulse beam in which, around its impact point on a workpiece consisting of one or more components, the pulse beam produces a welding plasma, said process comprising the steps of optically collecting only during the emission of a welding beam pulse at least one selected monochromatic emission line of the welding plasma from a major component of said workpiece;
converting the energy of said lines into analog electrical signals;

digitally processing said analog signals;
generating reference signals; and
comparing said processed signals with said reference signals to produce an indication of the depth of said weld.

2. A process according to claim 1, and including the additional steps of
developing a control signal that depends on the difference between the levels of said processed signals and said reference signals; and
controlling the power of said welding beam by said control signals.

3. An apparatus for the in-line inspection of the depth of a weld produced by a weld beam pulse from welding means in a workpiece consisting of one or more components, said welding means and said workpiece being contained in a welding enclosure, the improvement wherein said apparatus comprises
at least one inspection channel, each said channel including
optical means located in said enclosure for collecting radiation emitted by said plasma from said workpiece,
transmission means for transmitting radiation from said optical means exteriorly of said enclosure,
a monochromator connected to receive radiation transmitted by said transmission means from said optical means and pass at least one selected monochromatic emission line of the welding plasma from a major component of said workpiece, and
photomultiplier means connected to receive the output of said monochromator and produce corresponding electrical output signals;
means connected to receive and process the signals from the photomultiplier to produce processed signals so that only those photomultiplier signals produced during a welding beam pulse comprise said processed signals;
means for generating reference signals;
means for comparing said processed signals and said reference signals to produce an indication of the depth of said weld.

4. An apparatus according to claim 3, wherein the apparatus comprises an in-line control loop constituted by a signal supplied by an output of the comparison means, and controlling the intensity of the welding pulse beam.

5. An apparatus according to claim 3, wherein each said transmission means include an optical fiber connected between said optical means and said monochromator.

6. An apparatus according to claim 3, wherein each optical means comprise optical lenses and mirrors.

7. An apparatus according to claim 3, wherein each optical means comprise a collimator.

8. An apparatus according to claim 3
wherein said inspection channels are paired, and
said apparatus also includes control means for rendering equal the optoelectronic efficiency of the inspection channels of each pair.

9. An apparatus according to claim 8, wherein said control means are constituted by a radiation source emitting the same radiation in each of the inspection channels of the same pair.

10. An apparatus according to claim 3, wherein the processing means comprise means for standardizing the signals received from the inspection channels, a recorder permitting a delayed processing of these signals, a band-pass filter, a time filter, an analog-digital converter and an arithmetic unit.

* * * * *